US012329954B1

(12) United States Patent
Denyer et al.

(10) Patent No.: US 12,329,954 B1
(45) Date of Patent: Jun. 17, 2025

(54) MEDICAMENT DELIVERY DEVICE

(71) Applicant: Genzyme Corporation, Cambridge, MA (US)

(72) Inventors: Timothy Denyer, Melbourn (GB); James Bradford, Melbourn (GB); Alexander Hee-Hanson, Melbourn (GB); Robert Wilson, Melbourn (GB); Dean Twite, Melbourn (GB); Thomas Lever, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/819,704

(22) Filed: Aug. 29, 2024

(51) Int. Cl.
*A61M 5/32* (2006.01)
*A61M 5/315* (2006.01)

(52) U.S. Cl.
CPC .......... *A61M 5/3243* (2013.01); *A61M 5/315* (2013.01)

(58) Field of Classification Search
CPC .......... A61M 2005/31508; A61M 2005/3247; A61M 2205/27; A61M 2205/273; A61M 5/315; A61M 5/31501; A61M 5/31565; A61M 5/31566; A61M 5/31576; A61M 5/31583; A61M 5/31586; A61M 5/32; A61M 5/3202; A61M 5/3205; A61M 5/321; A61M 5/3243; A61M 5/3245; A61M 5/50
See application file for complete search history.

(56) References Cited

U.S. PATENT DOCUMENTS

| 4,118,611 | A | 10/1978 | Harris |
| 5,609,577 | A | 3/1997 | Haber et al. |
| 5,743,888 | A | 4/1998 | Wilkes et al. |
| 6,261,264 | B1 | 7/2001 | Tamaro |
| 10,765,811 | B2 * | 9/2020 | Vedrine ............... A61M 5/3137 |
| 10,926,040 | B2 * | 2/2021 | Karasawa ............... A61M 5/32 |
| 2004/0044318 | A1 | 3/2004 | Fiser et al. |
| 2005/0171477 | A1 | 8/2005 | Rubin et al. |

(Continued)

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.

(Continued)

Primary Examiner — Shefali D Patel
(74) Attorney, Agent, or Firm — Fish & Richardson P.C.

(57) ABSTRACT

A medicament delivery device comprises a housing, a needle, a needle cover, a needle cover biasing member, and a needle cover retaining mechanism. The needle cover is axially movable between an extended position and a retracted position. The needle cover biasing member is configured to bias the needle cover axially in a distal direction towards the extended position. The needle cover retaining mechanism is configured to be moved between a first state, in which the needle cover retaining mechanism is disengaged from the needle cover such that the needle cover is moveable in the distal direction under a force of the needle cover biasing member, and a second state, in which the needle cover retaining mechanism is configured to engage the needle cover and prevent distal movement of the needle cover under the force of the needle cover biasing member, when the needle cover is in the retracted position.

20 Claims, 8 Drawing Sheets

(56) References Cited

U.S. PATENT DOCUMENTS

| | | |
|---|---|---|
| 2011/0276029 A1 | 11/2011 | Field |
| 2012/0101475 A1 | 4/2012 | Wilmot et al. |
| 2016/0271319 A1 | 9/2016 | Bengtsson et al. |
| 2018/0200487 A1 | 7/2018 | Sokolski et al. |
| 2022/0288318 A1 | 9/2022 | Plambech et al. |
| 2024/0198013 A1 | 6/2024 | Laurence et al. |

OTHER PUBLICATIONS

Speciale et al., "Snap-Through Buckling Mechanism for Frequency-up Conversion in Piezoelectric Energy Harvesting," Applied Sciences, May 23, 2020, 10(10):3614, 18 pages.
U.S. Appl. No. 18/818,944, filed Aug. 29, 2024, Timothy Denyer.
U.S. Appl. No. 18/819,383, filed Aug. 29, 2024, Timothy Denyer.
U.S. Appl. No. 18/819,625, filed Aug. 29, 2024, Timothy Denyer.

\* cited by examiner

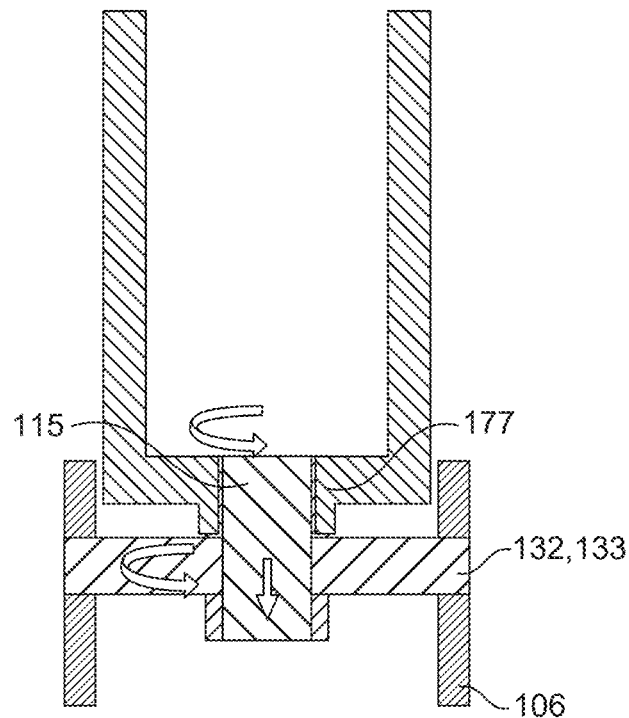
FIG. 7A
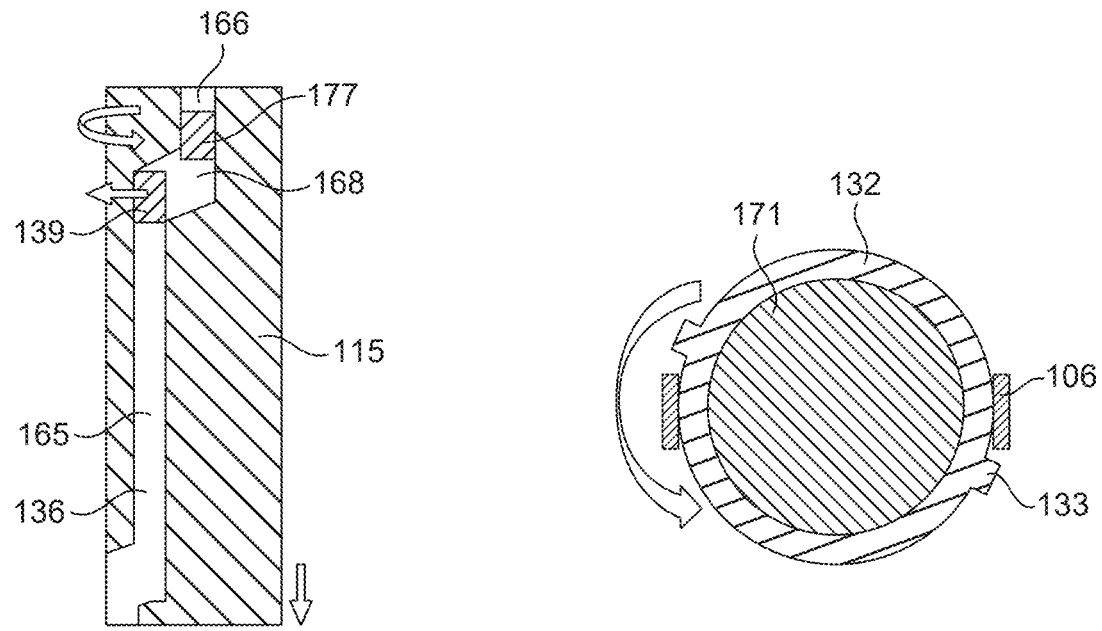
FIG. 7B
FIG. 7C

MEDICAMENT DELIVERY DEVICE

TECHNICAL FIELD

This application relates to a medicament delivery device.

BACKGROUND

Medicament delivery devices are used to deliver a range of medicaments.

In some devices, the device must be held in a holding position at an injection site for a predetermined period of time, to ensure that the correct dose of medicament is dispensed from the device, before removing the device from the injection site.

It may be difficult to hold the device in the holding position whilst the medicament is dispensed. This may result in pain, discomfort, a wet injection site, early device removal and/or partial delivery of the medicament.

The present disclosure provides an improved medicament delivery device.

SUMMARY

According to a first aspect of the present disclosure, there is provided a medicament delivery device comprising a housing comprising a proximal end and a distal end, a needle and a needle cover, wherein the needle cover is axially movable between an extended position, in which the needle cover extends from the distal end of the housing and covers a distal end of the needle, and a retracted position, in which the needle cover is located in a proximal position relative to the extended position such that the needle protrudes from a distal end of the needle cover, a needle cover biasing member configured to bias the needle cover axially in the distal direction towards the extended position, and a needle cover retaining mechanism configured to be moved between a first state, in which the needle cover retaining mechanism is disengaged from the needle cover such that the needle cover is moveable in the distal direction under the force of the needle cover biasing member, and a second state, in which the needle cover retaining mechanism is configured to engage the needle cover and prevent distal movement of the needle cover under the force of the needle cover biasing member, when the needle cover is in the retracted position.

One advantage of the described techniques in the present disclosure is that the biasing force of the needle cover biasing member can be completely eliminated whilst the needle cover retaining mechanism is engaged. Thus, the force required to be applied by an operator to activate and hold the medicament delivery device can be completely removed. Thus, those who have difficulty maintaining a high hold force throughout the injection duration will find using the medicament delivery device described in the present disclosure easier to operate.

In some embodiments, the needle cover retaining mechanism may comprise a retaining member, the retaining member being rotatable between a first rotational position where the retaining member is in the first state, in which the retaining member is disengaged with the needle cover to allow axial movement of the needle cover, and a second rotational position where the retaining member is in the second state, in which the retaining member is engaged with the needle cover to prevent axial movement of the needle cover.

Thus, release of the needle cover and the ability of the needle cover biasing member to biasing the needle cover into the extended position can be accurately controlled. By utilising rotation, especially rotation about the longitudinal axis of the device, to move the retaining member from between the first and second states, the medicament delivery device can be more compact as there is no need to accommodate space between other components for axial movement of the release element.

In some embodiments, the needle cover retaining mechanism may further comprise a proximally extending arm of the needle cover, a proximal end of the arm may be located distally of the retaining member when the needle cover is in the extended position and the proximal end of the arm may be located proximally of the retaining member when the needle cover is in the retracted position.

Thus, the arm of the needle cover can be engaged by the retaining member when the needle cover is moved into the retracted position.

In some embodiments, the arm of the needle cover may comprise a recess configured to receive the retaining member when the needle cover is in the retracted position and the retaining member is in the second rotational position.

In some embodiments, the recess in the arm of the needle cover may define a latch portion located proximally of the recess, the latch portion may comprise an engaging surface configured to abut a proximally facing surface of the retaining member when the needle cover is in the retracted position and the retaining member is in the second rotational position.

Thus, the location of the retaining member in the recess of the arm of the needle cover ensure engaging contact between the retaining member and the needle cover. As a result, the biasing force of the needle cover biasing member is transferred to the retaining member via contact between the retaining member in the recess of the arm and the latch of the arm of the needle cover. Therefore, the needle cover biasing member is prevented from extending by the engagement with the retaining member rather than by a holding force exerted by an operator. The latch ensures a larger contact area to ensure engaging contact.

In some embodiments, the retaining member may comprise a flat plate. The flat plate may comprise a central aperture.

Thus, the retaining member takes up minimal space within the medicament delivery device. The central aperture may allow for other components of the medicament delivery device to be moved axially through the retaining member.

In some embodiments, the flat plate may be generally circular and may comprise a cut-out section configured to allow the arm of the needle cover to be moved proximally past the flat plate when the retaining member is in its first rotational position.

In some embodiments, the cut-out section may comprise a radially extending first side wall configured to provide a step-change in the radius of the retaining member that defines the engaging portion.

In some embodiments, the medicament delivery device may further comprise a drive mechanism, the drive mechanism may comprise a drive member and a plunger rod configured to move from a proximal position to a distal position under the force of the drive member, the needle cover retaining mechanism may be in the first state when the plunger rod is in the proximal and distal positions and may be in the second state for at least a majority of the length of the plunger rod stroke between the proximal and distal positions.

In some embodiments, the plunger rod may comprise a slot having first, second, and third portions extending longitudinally, the portions of the slot may be circumferentially offset from one another and joined by first and second connecting portions.

In some embodiments, the retaining member may comprise a protrusion located in the slot, the slot and protrusion may be configured to allow relative axial movement between the plunger rod and the retaining member.

Thus, the plunger rod can be moved axially without axial movement of the retaining element or needle cover. The prevents premature movement of the needle cover towards the extended position. Thus, there is no additional biasing force added to the needle cover during movement of the plunger rod. In addition, the engagement of the protrusion in the slot allows for the rotational position of the plunger rod to automatically engage and disengage the retaining mechanism, which reduces the mental load on an operator.

In some embodiments, when the plunger rod is in the proximal position the protrusion of the retaining member may be located in the first portion of the slot, and upon distal movement of the plunger rod from the proximal position the protrusion may be moved into the second portion of the slot such that the retaining member is moved from the first state to the second state and rotationally coupled to the plunger rod.

Thus, the projection of the drive member housing is in the second portion of the slot when the protrusion of the retaining member is in the first portion of the slot. Therefore, as the drive member causes the plunger rod to move axially in the distal direction, the protrusion of the retaining member is caused to move from the first state in the first rotational position to the second state in the second rotational position to engage with the arm of the needle cover to prevent the needle cover biasing member from extending distally.

In some embodiments, when the plunger rod is moved into the distal position, the protrusion of the retaining member may be located in the second portion of the slot and the plunger rod may be rotatable between a first plunger rod rotational position and a second plunger rotational position to move the retaining member from the second state to the first state.

Thus, the rotational position of the release element is fixed to the rotational position of the plunger rod for the remainder of the stroke once the plunger rod has moved from its proximal position. This means that, after engagement, the retaining member is only disengaged from the needle cover at a predetermined position of the plunger rod at the end of the plunger rod stroke.

In some embodiments, the drive mechanism may further comprise a drive member housing, the drive member housing may comprise a projection located in the slot of the plunger rod, wherein the projection may be located in the second portion of the slot for the majority of the plunger rod stroke from the proximal position such that the plunger rod is maintained in the first plunger rod rotational position, and wherein the projection is located in the third portion of the slot when the plunger rod is in the distal position such that the plunger rod is moved to the second plunger rod rotational position.

Thus, movement of the plunger rod from the first plunger rod rotational position to the second plunger rod rotational position at the distal position of the plunger rod at the end of the plunger rod stroke can cause the release member to move from the second state in the second rotational position to the first state in the first rotational position and release the needle cover so that the needle cover biasing member can bias the needle cover in the distal direction towards the extended position.

In some embodiments, engagement between the projection of the drive member housing and the second connecting portion of the slot induces the plunger rod to rotate from its first rotational position to its second rotational position as the plunger rod is moved axially into its distal position.

Thus, the projection of the drive member housing reaches the third portion of the slot first. Therefore, as the projection of the drive member housing causes the plunger rod to rotate, the protrusion of the retaining member in the second portion of the slot causes the retaining member to rotate with the plunger rod from the second state in the second rotational position to the first state in the first rotational position to disengage with the arm of the needle cover to allow the needle cover biasing member to extend distally.

In some embodiments, the projection of the drive member housing may be located proximally to the protrusion of the retaining member.

In some embodiments, the drive mechanism may further comprise a rotating collar located at least partially within the drive member housing, the rotating collar may comprise a threaded surface, the plunger rod may comprise a threaded surface configured to cooperate with the threaded surface of the rotating collar, and the drive member may comprise a torsion spring.

Thus, the space required to house the drive mechanism can be reduced, especially after use, and can be located proximally. In addition, the rotational motion of the rotating collar can be transformed into axial motion of the plunger.

In some embodiments, the medicament delivery device may be configured to inject greater than 2 ml of medicament and/or wherein the medicament delivery device is configured to inject medicament having a viscosity of greater than 25 cP.

In some embodiments, the medicament delivery device may further comprise a needle cover lock configured to prevent proximal movement of the needle cover once the needle cover is in the extended position post-use.

Therefore, after us, the needle cover may permanently cover the needle to prevent an accidental contact with the used needle.

In some embodiments, the medicament delivery device may comprise medicament.

The medicament delivery device may comprise a container for containing the medicament. The medicament may be located in the container. The container may be a syringe. The syringe may comprise the needle. The container may be a cartridge which is initially separated from the needle when the needle cover is in the extended position.

In a second aspect of the present disclosure, there is provided a method of temporarily removing the holding force required to operate a medicament delivery device (100), the method comprising moving a needle cover from an extended position, in which the needle cover extends from the distal end of a housing and covers a distal end of a needle, to a retracted position, in which the needle protrudes from a distal end of the needle cover, against the force of a needle cover biasing member, rotating a retaining member of a retaining mechanism from a first state, in which the retaining member is disengaged from the needle cover, and a second state, in which the retaining member engages the needle cover and prevents distal movement of the needle cover under the force of the needle cover biasing member, such that a user is no longer required to counteract the needle cover biasing member force, rotating the retaining member from the second state back to the first state to reapply the force of the needle cover biasing member, moving the needle cover from the retracted position to the extended position.

BRIEF DESCRIPTION OF THE FIGURES

Embodiments will now be described, by way of example only, with reference to the accompanying drawings, in which:

FIGS. 7A to 7C show various views of components of a medicament delivery device in a post-dose configuration.

DETAILED DESCRIPTION

Figure 1A:
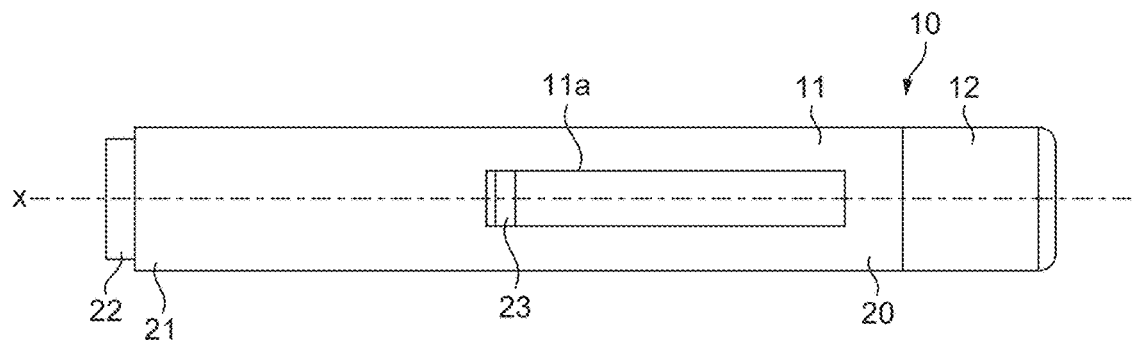
FIG. 1A shows an injector device with a cap attached.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
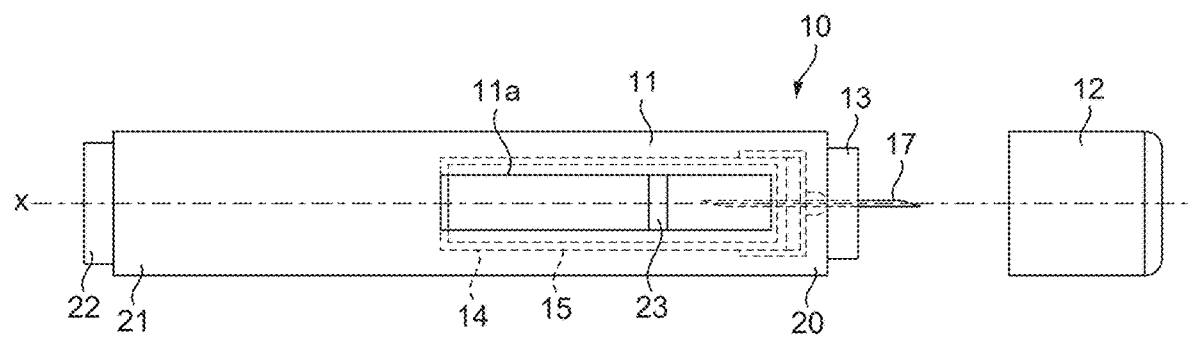
FIG. 1B shows the injector device of FIG. 1A with the cap removed.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11. Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2:
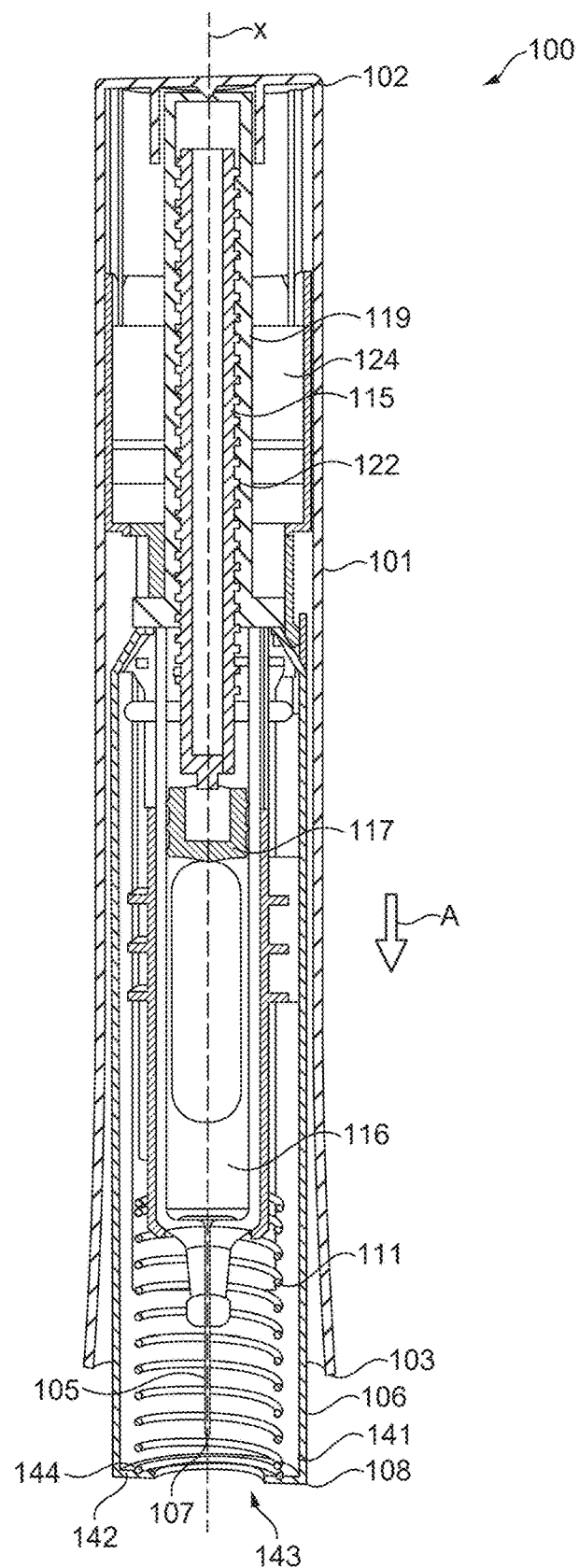
FIG. 2 shows a simplified schematic cross-sectional side view of a medicament delivery device.

FIG. 2 shows a simplified view of a medicament delivery device 100. The medicament delivery device 100 comprises a housing 101. The housing 101 comprises a proximal end 102 and a distal end 103. The medicament delivery device 101 further comprises a needle 105 for injecting medicament and a needle cover 106. The needle 105 has a distal end 107. The needle cover 106 is axially movable relative to the housing 101 between an extended position, in which the needle cover 106 extends from the distal end 103 of the housing 101 and covers the distal end 107 of the needle 105, and a retracted position, in which the needle cover 106 is located in a proximal position relative to the extend position such that the needle 105 protrudes from a distal end 108 of the needle cover 106 . . . . The medicament delivery device 100 extends along an axis X.

The medicament delivery device 100 is shown in the extended position in FIG. 2. The extended position may be the initial position in which the medicament delivery device 100 is provided.

The medicament delivery device 100 further comprises a needle cover biasing member 111. The needle cover biasing member 111 is configured to bias the needle cover 106 axially in the distal direction towards the extended position. The distal direction is indicated by the direction of the arrow A in FIG. 2. In some embodiments, the needle cover biasing member 111 may be a spring.

The medicament delivery device 100 may further comprise a plunger rod 115. The plunger rod 115 may be axially moveable within the housing 101. The medicament delivery device 100 may further comprise a syringe 116. The syringe 116 may be configured to contain medicament. The syringe 116 may comprise the needle 105 located on a distal end of the syringe 116. The plunger rod 115 may be axially movable within a syringe 116 of the medicament delivery device 100 to dispense medicament from the syringe 116 via the needle 105. The syringe 116 may comprise a piston 117. The plunger rod 115 may act on the piston to dispense medicament from the syringe 116 via the needle 105.

The medicament delivery device 100 may further comprise a collar 119. The collar 119 may be axially fixed relative to the housing 101. The collar 119 may interfaces with the plunger rod 115 via a screw thread 122. The medicament delivery device 100 may further comprise a drive member 124. The drive member 124 may be a biasing member that is configured to rotate the collar 119 when the drive member 124 is released. The drive member 124 may be a rotational biasing member, such as a spring. The spring 124 may be a torsion spring. The torsion spring 124 may be released when the needle cover 106 reaches a predetermined axial displacement in the proximal direction with a release mechanism (not shown). The rotation of the collar 119 may cause the plunger rod 115 to move distally within the syringe 116, in view of the screw thread 122, to thereby dispense medicament from the syringe 116 via the needle 105.

The needle cover 106 may be moved axially into the housing 101 uncovering the needle 105. The needle cover 106 may be moved proximally by being pressed against an injection site 125. The proximal axial displacement of the needle cover 106 may cause the release of the spring 124 which rotates the collar 119. The rotation of the collar 119 may move the plunger rod 115 axially in the distal direction within the syringe 116 to dispense the medicament via the needle 105.

The medicament delivery device 100 may be pressed against the injection site 125, to hold the needle cover 106 in the retracted position whilst the medicament is dispensed from the medicament delivery device 100. In known medicament delivery devices, the user must hold the medicament delivery device 100 against the injection site 125 against the force of the needle cover biasing member 111.

After the medicament has been dispensed, the medicament delivery device 100 is removed from the injection site 125. The needle cover 106 may move distally under the force of the needle cover biasing member 111 to a locked position. In the locked position, the needle cover 106 covers the distal end 107 of the needle 105. In the locked position, the needle cover 106 may be prevented from moving proximally.

The medicament delivery device 100 may be configured to inject greater than 2 ml of medicament and/or the medicament delivery device 100 is configured to inject medicament having a viscosity of greater than 25 cP.

A medicament delivery device 100 according to the present disclosure may be generally similar to the medicament delivery device previously described but with the additional of a needle cover retaining mechanism 131.

Figure 3A:
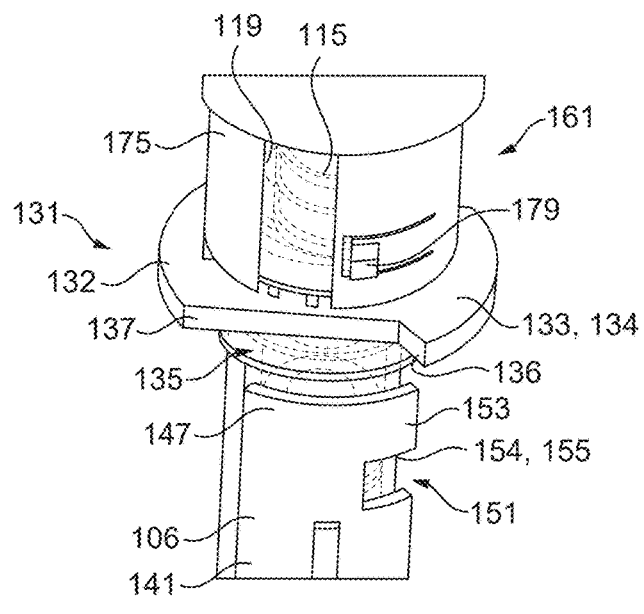
FIGS. 3A to 3C show simplified schematic perspective views of a retaining mechanism and drive mechanism of a medicament delivery device at various stages of operation.
Figure 3B:
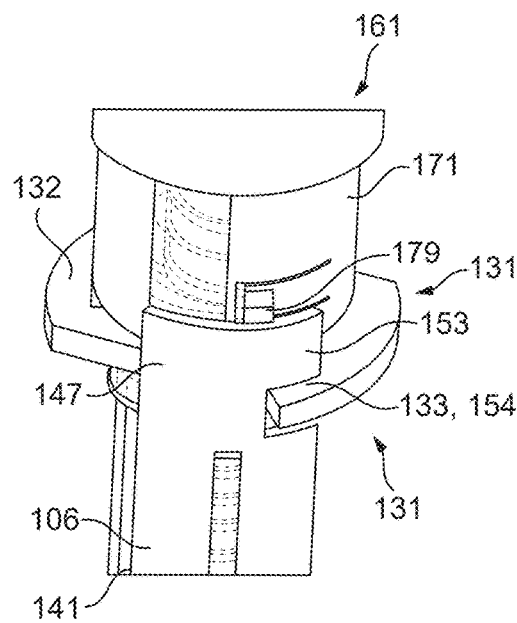
Figure 3C:
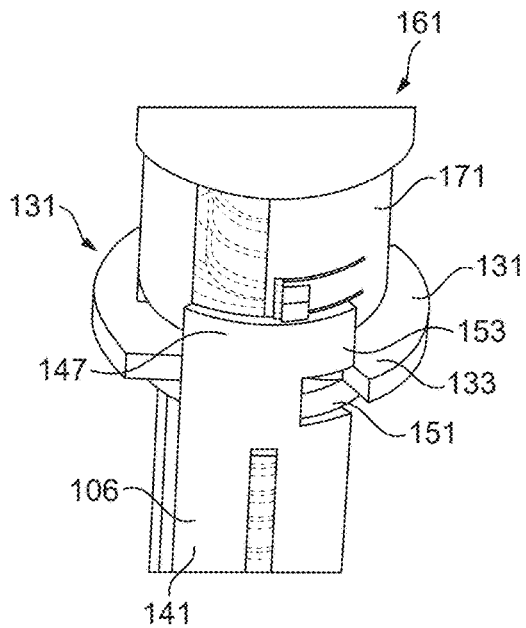

FIGS. 3A to 3C show a simplified view of a needle cover retaining mechanism 131 according to the present disclosure. The needle cover retaining mechanism 131 is configured to be moved between a first state, shown in FIG. 3A and FIG. 3C, and a second state, shown in FIG. 3B, when the needle cover 106 is in the retracted position. In the first state, the needle cover retaining mechanism 131 is disengaged from the needle cover 106. When the needle cover retaining mechanism 131 is disengaged from the needle cover 106, the needle cover is moveable in the distal direction under the force of the needle cover biasing member 111. In the second state, the needle cover retaining mechanism 131 is engaged with the needle cover 106. When the needle cover retaining mechanism 131 is engaged with the needle cover, the needle cover retaining mechanism 131 is configured to prevent distal movement of the needle cover 106 under the force of the needle cover biasing member 111.

One advantage of the techniques described in the present disclosure is that the biasing force of the needle cover biasing member 111 can be completely eliminated whilst the needle cover retaining mechanism 131 is engaged. Thus, the force required to be applied by an operator to activate and hold the medicament delivery device 100 can be completely removed. Thus, those who have difficulty maintaining a high hold force throughout the injection duration will find using the medicament delivery device 100 described in the present disclosure easier to operate.

As shown in FIGS. 3A to 3C, the needle cover retaining mechanism 131 may comprise a retaining member 132. The retaining member 132 may be rotatable between a first rotational position, shown in FIGS. 3A and 3C, and a second rotational position, shown in FIG. 3B. When the retaining member 132 is in the first rotational position the retaining member 132 may be in the first state, and when the retaining member 132 is in the second rotational position the retaining member 132 may be in the second state. In the first state, the retaining member 132 may be disengaged with the needle cover 106. Therefore, in the first state, the retaining member 132 may allow axial movement of the needle cover 106. When the needle cover 106 is held against the injection site, the retaining member 132 may allow the biasing force of the needle cover biasing member 111 to biasing the needle cover 106 against the injection site. This is the force that must be overcome by the operator's hold force during use of the medicament delivery device 100.

The retaining member 132 may be located proximally of the needle cover 106 when the needle cover 106 is in its extended position, as shown in FIG. 3A. The retaining member 132 may comprise an engaging portion 133. The engaging portion 133 of the retaining member 132 may be configured to engage with the needle cover 106, when the needle cover 106 is in the retracted position and the retaining member 132 is moved to the second rotational position, as shown in FIG. 3B. The engaging portion 133 may be formed by a proximally facing surface 134 of the retaining member 132. In some embodiments, the proximally facing surface 134 of the retaining member 132 may be the proximal-most surface of the retaining member 132.

The retaining member 132 may comprise a flat plate. In some embodiments, the retaining member 132 may be generally circular. The retaining member 132 may comprise a cut-out section 135. The cut-out section 135 may be defined by a first side wall 136 and a second side wall 137. The first side wall 136 may extend generally radially. The second side wall 137 may extend in a chord-like fashion from a point on the outer edge of the retaining member 132 to a point where it meets the first side wall 136. Thus, the cut-out section 135 may provide the retaining member 132 with an engaging portion 133 defined by a step-change in radius of the retaining member 132.

Figure 5A:
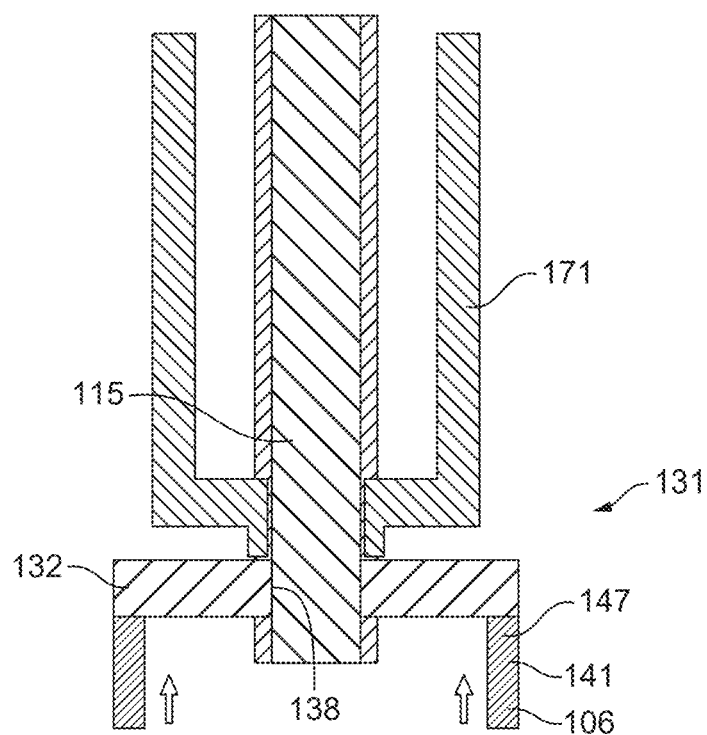
FIGS. 5A to 5C show various views of components of a medicament delivery device in a pre-use configuration.

The retaining member 132 may comprise an aperture 138, shown in FIG. 5A. The aperture 138 may be located centrally in the retaining member 132. The aperture 138 may extend fully through the thickness of the retaining member 132 in a direction parallel to the longitudinal axis X of the medicament delivery device 100. The aperture 138 may be configured to allow the plunger rod 115 to extend therethrough.

The retaining member 132 may be rotationally coupled to the plunger rod 115, as will be described in more detail hereinafter. The retaining member 132 may comprise a protrusion 139 shown in FIG. 5B. The protrusion 139 may be configured to engage with a feature of the plunger rod 115. The protrusion 139 of the retaining member 132 may extend radially from an inner periphery of the retaining member 132. That is, the protrusion 139 may extend radially inwards into the aperture 138.

The needle cover retaining mechanism 131 may further comprise an arm 141 of the needle cover 106. The arm 141 of the needle cover 106 may extend in the proximal direction.

The needle cover 106 may comprise a distal end portion 142, as shown in FIG. 2. The distal end portion 142 of the needle cover 106 may be the distal-most portion of the needle cover 306. The distal end portion may extend circumferentially around the central longitudinally axis X of the medicament delivery device 100. The distal end portion 142 of the needle cover 106 may be configured to prevent access to the needle 105 when the needle cover 106 is in the extended position. This may help prevent accidental contact with the needle 105.

The distal end portion 142 of the needle cover 106 may be annular. That is, the distal end portion 142 of the needle cover 106 may comprise an aperture 143, shown in FIG. 2. The aperture 143 may be located centrally in the distal end portion 142 of the needle cover 106. The aperture 143 may extend through the full thickness of the distal end portion 142 in the longitudinal direction. The aperture 143 may be configured to allow the needle 105 to extend therethrough when the needle cover 106 is in the retracted position.

The arm 141 of the needle cover 106 may extend in the proximal direction. That is, the arm 141 of the needle cover 106 may extend proximally from the distal end portion 142 of the needle cover 106. The arm 141 of the needle cover 106 may extend from a proximally facing surface 144 of the distal end portion 142 of the needle cover 106. The arm 141 may extend from the periphery of the proximally facing surface 144 of the distal end portion 142 of the needle cover 106.

The arm 141 may comprise a proximal end 147 spaced from the distal end portion 142 of the needle cover 106. The proximal end 147 of the arm 141 may be located distally of the retaining member 132 when the needle cover 106 is in the extended position. The proximal end 147 of the arm 141 may be located proximally of the retaining member 142 when the needle cover 106 is in the retracted position.

The needle cover 106 may comprise a recess 151. The recess 151 may be located in the proximal end 147 of the arm 141 of the needle cover 106. The recess 151 may be configured to receive the retaining member 132 when the needle cover 106 is in the retracted position and the retaining member 132 is in its second rotational position, as shown in FIG. 3B.

The recess 151 may extend in the circumferentially about the longitudinal axis X of the medicament delivery device 100 through a part of the arm 141 of the needle cover 106. The recess 151 may form a retaining member receiving slot. The recess 1451 in the arm 141 of the needle cover 106 may define a latch portion 153. The latch portion 153 of the arm 141 may be located proximally of the recess 151. The latch portion 153 may comprise an engaging surface 154. The engaging surface 154 of the latch portion 153 may be configured to abut the proximally facing surface 134 of the retaining member 132 when the needle cover 106 is in the retracted position and the retaining member 132 is in the second rotational position, as shown in FIG. 3B. The engaging surface 154 of the latch portion 153 of the arm 141 may be formed by a distally facing surface 155.

The medicament delivery device 100 of the present disclosure may further comprise a drive mechanism 161, as shown in FIGS. 3A to 3C. The drive mechanism 161 may comprise a drive member 124 and a plunger rod 115. In some embodiments, the drive member 124 may be a torsion spring.

The plunger rod 115 may be configured to move from a proximal position to a distal position under the force of the drive member 124. The needle cover retaining mechanism 131 may be in the first state when the plunger rod 115 is in the proximal and distal positions. The needle cover retaining mechanism 131 may be in the second state when the plunger rod 115 is between the proximal and distal positions. In some embodiments, the needle cover retaining mechanism 131 may be in the second state for at least a majority of the length of the plunger rod 115 stroke between the proximal and distal positions.

Figure 4:
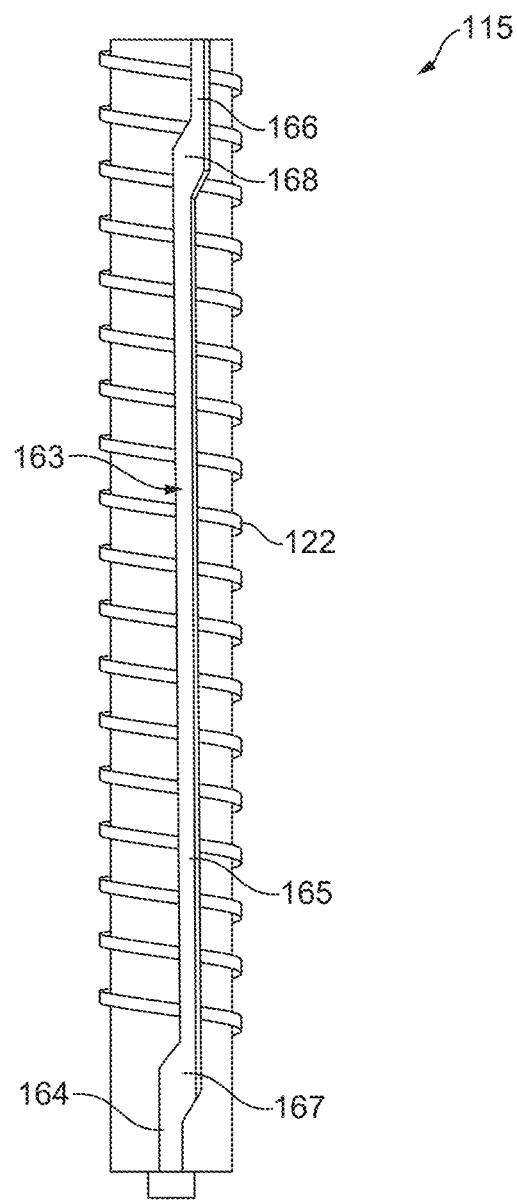
FIG. 4 shows a schematic side view of a plunger rod of a medicament delivery device.

Referring briefly to FIG. 4, a schematic side view of a plunger rod 115 of the present disclosure is shown. The plunger rod 115 may be generally cylindrical. The plunger rod 115 may be rotatable between a first rotational position and a second rotational position, as will be described in more detail hereinafter. The plunger rod 115 may be rotated into the second rotational position when the plunger rod 115 is moved into its distal position. It will be appreciated that movement of the plunger rod 115 from its first rotational position to its second rotational position may begin immediately prior to the plunger rod 115 reaching its distal position.

The plunger rod 115 may comprise a slot 163. The slot 163 may be formed in the outer circumferential surface of the plunger rod 115. The slot 163 may extend generally longitudinally. The slot 163 may extend generally along at least a majority of the length of the plunger rod 115. In some embodiments, the slot 115 may extend substantially the whole length of the plunger rod 115.

The slot 163 may comprise a first portion 164. The first portion 164 of the slot 163 may extend longitudinally. The first portion 164 of the slot 163 may extend from the distal end of the plunger rod 115 in a proximal direction.

The slot 163 may further comprise a second portion 165. The second portion 165 of the slot 163 may extend longitudinally. The second portion 165 of the slot 163 may extend from a region proximally adjacent the distal end of the plunger rod 115 to a region distally adjacent the proximal end of the plunger rod 115. The second portion 165 of the slot 163 may be offset from the first portion 164 of the slot 163. That is, the second portion 165 of the slot 163 may be circumferentially spaced from the first portion 164 of the slot 163.

The slot 163 may further comprise a third portion 166. The third portion 166 of the slot 163 may extend longitudinally. The third portion 166 of the slot 163 may extend from the proximal end of the plunger rod 115 in a distal direction. The third portion 166 of the slot 163 may be offset from the first portion 164 and the second portion 165 of the slot 163. That is, the third portion 166 of the slot 163 may be circumferentially spaced from the first portion 164 and the second portion 165 of the slot 163.

The circumferential distance between the first and second portion 164, 165 of the slot 163 may be the same as the circumferential distance between the second and third portions 165, 166 of the slot 163. The first portion 164 of the slot 163 may be located on the opposing side of the second portion of 165 of the slot 163 to the third portion 166 of the slot 163. In some embodiments, the second portion 165 of the slot 163 may overlap the proximal end of the first portion 164 of the slot 163 and the proximal end of the third portion 166 of the slot 163 in the axial direction, whilst being circumferentially spaced.

The slot 163 may further comprise a first connecting portion 167. The first connecting portion 167 of the slot 163 may connect the first and second portions 164, 165 of the slot 163. That is, the first connecting portion 167 of the slot 163 may connect the proximal end of the first portion 164 of the slot 163 to the distal end of the second portion 165 of the slot 163. The first connecting portion 167 of the slot 163 may extend at an inclined angle to the longitudinal axis X of the medicament delivery device 100 in a circumferential direction. That is, the first connecting portion 167 of the slot 163 may extend helically about the outer surface of the plunger rod 115.

The slot 163 may further comprise a second connecting portion 168. The second connecting portion 168 of the slot 163 may connect the second and third portions 165, 166 of the slot 163. That is, the second connecting portion 168 of the slot 163 may connect the proximal end of the second portion 165 of the slot 163 to the distal end of the third portion 166 of the slot 163. The second connecting portion 168 of the slot 163 may extend at an inclined angle to the longitudinal axis X of the medicament delivery device 100 in a circumferential direction. That is, the second connecting portion 168 of the slot 163 may extend helically about the outer surface of the plunger rod 115. In some embodiments, the inclined angle of the first and second connecting portions 167, 168 of the slot 163 may be equal.

The protrusion 139 of the retaining member 132 may be located in the slot 163 in the plunger rod 115, as will be explained in more detail hereinafter. The protrusion 139 and the slot 163 may be configured to allow relative axial movement between the plunger rod 115 and the release element 132 over at least an initial section of the plunger rod 115 stroke.

When the plunger rod 115 is in the proximal position, the protrusion 139 of the retaining member 132 may be located in the first portion 164 of the slot 163. Upon distal movement of the plunger rod 115 from the proximal position, the protrusion 139 may be moved into the second portion 165 of the slot 163 such that the retaining member 132 is moved from the first state to the second state, and subsequently rotationally coupled to the plunger rod 115.

When the plunger rod 115 is moved to the distal position, the protrusion 139 of the retaining member 132 may be located in the second portion 165 of the slot 163. Therefore, when the plunger rod 115 is rotated from its first rotational position to its second rotational position, the retaining member 132 may be moved from its second state to its first state.

Referring back to FIGS. 3A to 3C, the drive mechanism 161 may further comprise a drive member housing 171. The drive member housing 171 may be configured to at least partially house the drive member 124 of the drive mechanism 161. The drive member housing 171 may be located proximally of the retaining member 132. In some embodiments, the drive member housing 171 may be located proximate to the proximate end 102 of the housing 101. The drive member housing 171 may be rotationally fixed within the housing 101. In some embodiments, the drive member housing 171 may be axially fixed within the housing 101.

The drive member housing 171 may be generally cylindrical. The drive member housing 171 may comprises a distal end portion 173. The distal end portion 173 may extend perpendicularly to the longitudinal axis of the medicament delivery device 100. The distal end portion 173 of the drive member housing 171 may extend circumferentially around the central longitudinal axis X of the medicament delivery device 100.

The distal end portion 173 of the drive member housing 171 may be annular. That is, the distal end portion 173 of the drive member housing 171 may comprise an aperture 174. The aperture 174 may be located centrally in the distal end portion 173 of the drive member housing 171. The aperture 174 may extend through the full thickness of the distal end portion 173 of the drive member housing 171 in the longitudinal direction. The aperture 174 may be configured to allow the plunger rod 115 to move axially therethrough.

The drive member housing 171 may further comprise a side wall 175. The side wall 175 may be a circumferentially extending wall 175. The circumferentially extending side wall 175 may extend from a proximally facing surface of the distal end portion 173 in the proximal direction. The circumferentially extending side wall 175 may extend from an outer periphery of the proximally facing surface of the distal end portion 173. The side wall 175 may define a chamber for housing components of the drive mechanism 161.

The drive member housing 171 may further comprise a projection 177, best shown in FIG. 7A. The projection 177 may be configured to be located in the slot 163 of the plunger rod 115, as will be explained in more detail hereinafter. In some embodiments, the projection 177 may extend radially from an inner periphery of the drive member housing 171. The projection 177 may extend radially inwards into the aperture 174 in the distal end portion 173 of the drive member housing 171.

Figure 5B:
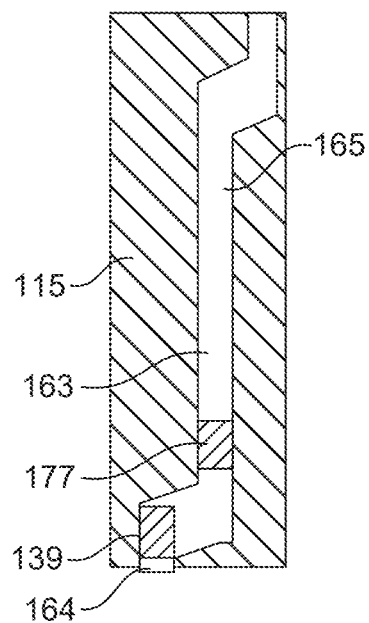

As shown in FIG. 5B, the projection 177 of the drive member housing 171 may be located in the slot 163 of the plunger rod 115. The projection 177 of the drive member housing 171 may be located in the slot 163 proximally relative to the location of the protrusion 139 in the slot 163 of the plunger rod 115. The projection 177 and slot 163 may be configured to allow axial relative movement between the plunger rod 115 and the drive member housing 171. Due to the geometry of the slot 163 in the plunger rod 115, the projection 177 and slot 163 may also be configured to cause the plunger rod 115 to move into its second rotational position as the plunger rod 115 reaches its distal position.

The projection 177 of the drive member housing 171 may be located in the second portion 165 of the slot 163 in the plunger rod 115 for the majority of the plunger rod 115 stroke from the proximal position to the distal position such that the plunger rod 115 is maintained in its first rotational position. The projection 177 of the drive member housing 171 may be located in the third portion 166 of the slot 163 in the plunger rod 115 when the plunger rod 115 is in the distal position such that the plunger rod 115 is moved to the second rotational position. Due to the location of the protrusion 139 of the retaining member 132 being located in the second portion 165 of the slot 163, movement of the plunger rod 115 from the first rotational position to the second rotational position may cause the retaining member 132 to move from its second state to its first state.

The drive member housing 171 may further comprise a stop 179. The stop 179 may comprise a projection extending radially outwards from the side wall of drive member housing 171. The stop 179 may be configured to limit proximal movement of the needle cover 106. Therefore, the recess 151 in the arm 144 of the needle cover 106 may be correctly positioned to receive the retaining member 132 when the retaining member 132 is moved to its second state when the needle cover 106 is in its retracted position.

Referring back to FIGS. 3A to 3C, the drive mechanism 161 may further comprise a collar 119. The collar 119 may be at least partially located in the drive member housing 171. The collar 119 may be axially fixed relative to the drive member housing 171. The collar 119 may be configured to rotate. The rotating collar 119 may comprise a screw thread 122. The screw thread 122 may form a threaded surface of the collar 119. The threaded surface may be an inner surface of the collar 119. As shown in FIG. 4, the plunger rod 115 may also comprise a screw thread 122. That is, the outer surface of the plunger rod 115 may comprise a screw thread 122. The threaded surface 122 of the collar 119 and the threaded surface 122 of the plunger rod 115 may be configured to cooperate.

When the drive member 124 is actuated, the drive member 124 may be configured to rotate the collar 119. Cooperation between the threaded surfaces 122 on the collar 119 and the plunger rod 115 may transform the rotational motion of the collar 119 into axial displacement of the plunger rod 115 in the distal direction.

Referring now to FIG. 5A to FIG. 8C, operation of the medicament delivery device 100 and the relationships between the features of the medicament delivery device 100 will now be described in further detail.

Figure 5C:
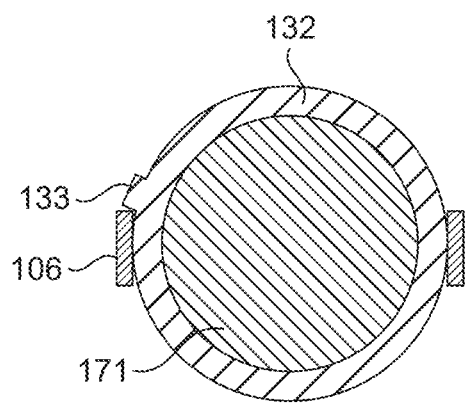

Referring to FIGS. 5A to 5C, a schematic cross-sectional side view of the needle cover retaining mechanism 131 and the drive mechanism 161 of the medicament delivery device 100 in its pre-use configuration, a schematic side view of the plunger rod 115 in its proximal position, and a top view of the retaining mechanism 131 in its first state, are shown, respectively.

FIGS. 5A to 5C show the components of the medicament delivery device 100 in their pre-use configuration. The needle cover 106 may be located in its extended position. That is, the proximal end 147 of the arm 144 of the needle cover 106 may be located distally of the retaining member 132. The plunger rod 115 may be located in its proximal position. The plunger rod 115 may be located in its first rotational position. The retaining member 132 may be in its first state, as shown in FIG. 5C. Thus, the needle cover biasing member 111 is able to bias the needle cover 106 distally to retain the needle cover 106 in the extended position.

However, due to the retaining member 132 being in its first state, the needle cover 106 may be moved proximally, as indicated by the arrows in FIG. 5A, against the force of the needle cover biasing member 111 by pressing the medicament delivery device 100 against an injection site.

Referring to FIG. 5B, the projection 177 of the drive member housing 171 may be located in the second portion 165 of the slot 163 in the plunger rod 115, when the plunger rod 115 is in the proximal position. The protrusion 139 of the retaining member 132 may be located in the first portion 164 of the slot 163 in the plunger rod 115, when the plunger rod 115 is in the proximal position.

Figure 6A:
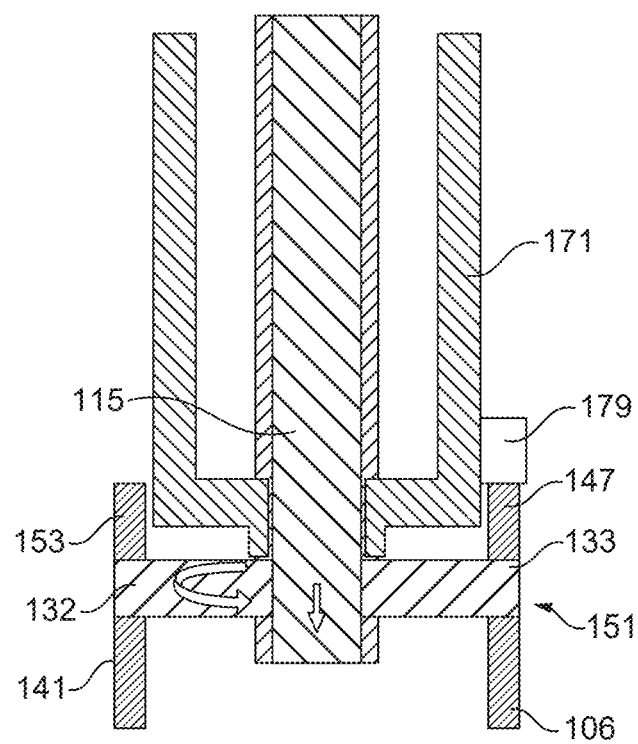
FIGS. 6A to 6C show various views of components of a medicament delivery device in a primed configuration.
Figure 6B:
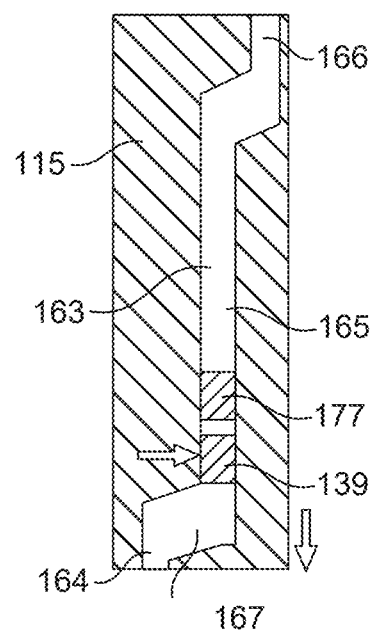
Figure 6C:
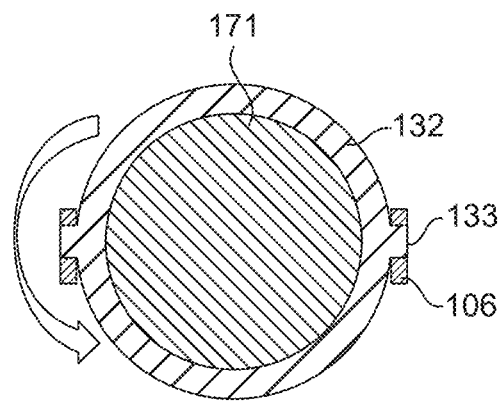

Referring to FIGS. 6A to 6C, a schematic cross-sectional side view of the needle cover retaining mechanism 131 and the drive mechanism 161 of the medicament delivery device 100 in its primed configuration, a schematic side view of the plunger rod 115 having moved from its proximal position, and a top view of the retaining mechanism 131 in its second state, are shown, respectively.

Referring to FIG. 6A, the needle cover 106 may have been moved into its retracted position against the biasing force of the needle cover biasing member 111. The proximal end 147 of the arm 144 of the needle cover 106 may be located proximally of the retaining member 132. In some embodiments, the proximal end 147 of the arm 144 of the needle cover 106 may abut the stop 179 of the drive member housing 171.

The plunger rod 115 may have been moved from its proximal position in the distal direction. Distal movement of the plunger rod 115 may cause the projection 177 of the drive member housing 171 to move along the second portion 165 of the slot 163 towards the third portion 166 of the slot 163. Distal movement of the plunger rod 115 may cause the protrusion 139 of the release member 132 to move into the second portion 165 of the slot 163. That is, upon initial distal movement of the plunger rod 115, the protrusion 139 may reach the proximal end of the first portion 164 of the slot 163 and be forced to rotate by its contact with the inclined first connecting portion 167 of the slot 163 until the protrusion 139 reaches the second portion 165 of the slot 163.

The distal movement of slot 163 forces the protrusion 139 from the first portion 164 of the slot 163 to the second portion 165 of the slot 163. Thus, the retaining member 132 is forced to rotate from its first state, shown in FIG. 3A, to its second state, shown in FIG. 3B. In its second state, the engaging portion 133 of the retaining member 132 may be located in the recess 151 of the arm 144 of the needle cover 106. The engaging surface 154 of the arm 144 of the needle cover 106 may abut the engaging portion 133 of the retaining member 132.

As a result, when in the second state, the retaining member 132 prevents distal movement of the needle cover 106 under the force of the needle cover biasing member 111. Furthermore, the biasing force of the needle cover biasing member 111 is transferred via the latch portion 153 to the retaining member 132 so that the holding force required by an operator is reduced, if not removed.

Referring to FIGS. 7A to 7C, a schematic cross-sectional side view of the needle cover retaining mechanism 131 and the drive mechanism 161 of the medicament delivery device 100 in its post-dose configuration, a schematic side view of the plunger rod 115 in its distal position, and a top view of the retaining mechanism 131 in its first state, are shown, respectively.

Referring to FIG. 7A, the needle cover 106 may still be located in its retracted position due to the medicament delivery device 100 being held against an injection site. The plunger rod 115 may be located in its distal position. The retaining member 132 may have returned to its first state.

Distal movement of the plunger rod 115 may cause the projection 177 of the drive member housing 171 to move into the third portion 166 of the slot 163. Distal movement of the plunger rod 115 may cause the protrusion 139 to move towards the proximal end of the plunger rod 115.

That is, upon the plunger rod 115 reaching its distal position, the distal movement of the plunger rod 115 against the projection 177 of the drive member housing 171 may cause the plunger rod 115 to rotate from its first rotational position, shown in FIG. 6B, to its second rotational position, shown in FIG. 7B. The projection 177 may reach the proximal end of the second portion 165 of the slot 163 and continued distal movement of the plunger rod 115 forces the plunger rod 115 to rotate by contact with the inclined second portion 168 of the slot 163 until the projection reaches the third portion 166 of the slot 163.

As a result of rotation of the plunger rod 115 from its first rotational position to its second rotational position, the protrusion 139 of the retaining member 132 which is located in the second portion 165 of the slot 163 is caused to rotate with the plunger rod 115. That is, the retaining member 132 and plunger rod 115 may be rotationally coupled whilst the protrusion 139 is located in the second portion 165 of the slot 163. Thus, the retaining member 132 is forced to rotate from its second state, shown in FIG. 3B, back to its first state, shown in FIG. 3C.

Figure 8A:
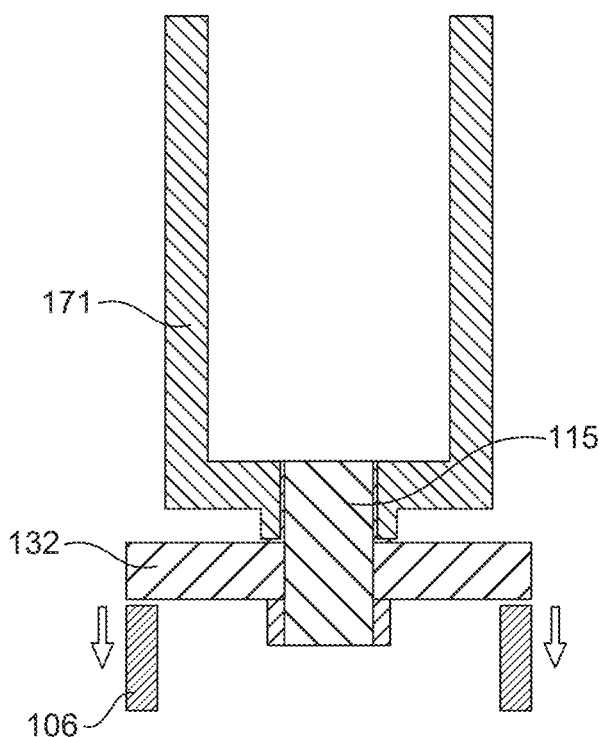
FIGS. 8A to 8C show various views of components of a medicament delivery device in a post-use configuration.
Figure 8B:
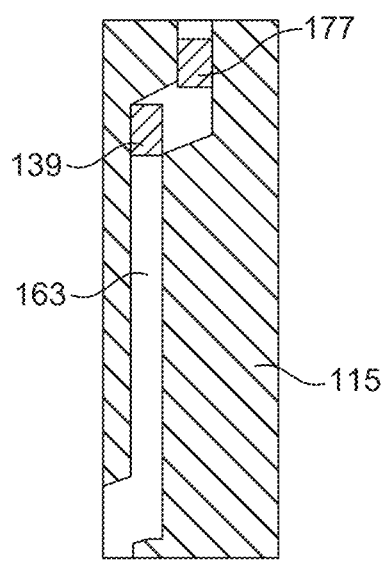
Figure 8C:
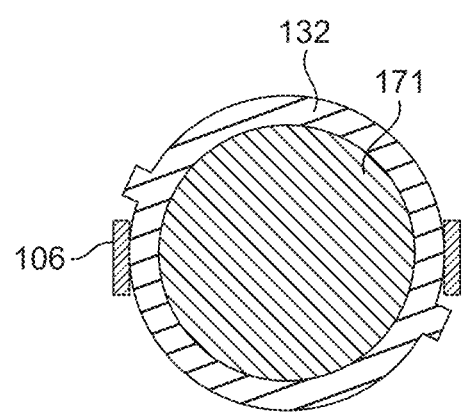

Rotation of the retaining member 132 back into its first state released the needle cover 106. Therefore, the needle cover biasing member 111 is allowed to bias the needle cover 106 back to the extended extend position when the medicament delivery device 100 is removed from an injection site, as shown in FIGS. 8A to 8C, in a post-use configuration. A needle cover lock may be engaged to prevent further proximal movement of the needle cover.

Although described previously in detail, a brief description of the method of temporarily removing the holding force required to operate a medicament delivery device 100 will be given. The method comprises moving a needle cover 106 from an extended position, in which the needle cover 106 extends from the distal end of a housing 101 and covers a distal end 107 of a needle 105, to a retracted position, in which the needle 105 protrudes from a distal end 108 of the needle cover 106, against the force of a needle cover biasing member 111.

The method further comprises rotating a retaining member 132 of a retaining mechanism 131 from a first state, in which the retaining member 132 is disengaged from the needle cover 106, and a second state, in which the retaining member 132 engages the needle cover 106 and prevents distal movement of the needle cover 106 under the force of the needle cover biasing member 111, such that a user is no longer required to counteract the needle cover biasing member force.

The method further comprises rotating the retaining member 132 from the second state back to the first state to reapply the force of the needle cover biasing member 111, and moving the needle cover 106 from the retracted position to the extended position.

The features described and/or contemplated in relation to the medicament delivery device 200 may be incorporated in another medicament delivery device, for example a medicament delivery device having a different mechanism for dispensing medicament to that described in relation to the medicament delivery device 100, and/or a medicament delivery device which is configured to inject 2 ml or less of medicament and/or a medicament delivery device which is configured to inject medicament having a viscosity of 25 cP or less, and/or a medicament delivery device in which the medicament is contained in a cartridge which is initially separated from the needle when the needle cover is in the initial position.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N—(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a caperturesterol-reducing antisense therapeutic for the treatment of familial hyper-caperturesterolemia or RG012 for the treatment of Alport syndrom. Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')$_2$ fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device.

Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

REFERENCE NUMERALS

10 Drug Delivery Device
11 Housing
12 Cap Assembly
13 Needle Sleeve
17 Needle
20 Distal Region
21 Proximal Region
22 Button
23 Piston
100 Medicament Delivery Device
101 Housing
102 Proximal End
103 Distal End 105 Needle
106 Needle Cover
107 Distal End
108 Distal End
111 Needle Cover Biasing Member
115 Plunger Rod
116 Syringe
117 Piston
119 Collar
122 Screw Thread
124 Drive Member
125 Injection Site
131 Needle Cover Retaining Mechanism
132 Retaining Member
133 Engaging Portion
134 Proximally Facing Surface
135 Cut-Out Section
136 First Side Wall
137 Second Side Wall
139 Protrusion
141 Arm
142 Distal End Portion
143 Aperture
144 Proximally Facing Surface
147 Proximal End
151 Recess
153 Latch Portion
154 Engaging Surface
155 Distally Facing Surface
161 Drive Mechanism
163 Slot
164 First Portion
165 Second Portion
166 Third Portion
167 First Connecting Portion
168 Second Connecting Portion
171 Drive Member Housing
173 Distal End Portion
174 Aperture
175 Side Wall
177 Projection
179 Stop

The invention claimed is:

1. A medicament delivery device comprising:
a housing comprising a proximal end and a distal end;
a needle and a needle cover,
wherein the needle cover is axially movable between an extended position, in which the needle cover extends from the distal end of the housing and covers a distal end of the needle, and a retracted position, in which the needle cover is located in a proximal position relative to the extended position such that the needle protrudes from a distal end of the needle cover;
a needle cover biasing member configured to bias the needle cover axially in a distal direction towards the extended position;
a needle cover retaining mechanism configured to be moved between a first state, in which the needle cover retaining mechanism is disengaged from the needle cover such that the needle cover is moveable in the distal direction under a force of the needle cover biasing member, and a second state, in which the needle cover retaining mechanism is configured to engage the needle cover and prevent distal movement of the needle cover under the force of the needle cover biasing member, when the needle cover is in the retracted position, wherein the needle cover retaining mechanism comprises a retaining member; and
a drive mechanism comprising a plunger rod, wherein the plunger rod is configured to cause the retaining member to (i) be moved from the first state into the second state and (ii) be rotationally coupled to the plunger rod upon distal movement of the plunger rod.

2. The medicament delivery device according to claim 1, wherein the retaining member is rotatable between a first rotational position where the retaining member is in the first state, in which the retaining member is disengaged with the needle cover to allow axial movement of the needle cover, and a second rotational position where the retaining member is in the second state, in which the retaining member is engaged with the needle cover to prevent the axial movement of the needle cover.

3. The medicament delivery device according to claim 2, wherein the needle cover retaining mechanism further comprises a proximally extending arm of the needle cover, wherein a proximal end of the arm is located distally of the retaining member when the needle cover is in the extended position and the proximal end of the arm is located proximally of the retaining member when the needle cover is in the retracted position.

4. The medicament delivery device according to claim 3, wherein the arm of the needle cover comprises a recess configured to receive the retaining member when the needle cover is in the retracted position and the retaining member is in the second rotational position.

5. The medicament delivery device according to claim 4, wherein the recess in the arm of the needle cover defines a latch portion located proximally of the recess, the latch portion comprising an engaging surface configured to abut a proximally facing surface of the retaining member when the needle cover is in the retracted position and the retaining member is in the second rotational position.

6. The medicament delivery device according to claim 4, wherein the retaining member comprises a flat plate.

7. The medicament delivery device according to claim 6, wherein the flat plate is generally circular and comprises a cut-out section configured to allow the arm of the needle cover to be moved proximally past the flat plate when the retaining member is in the first rotational position.

8. The medicament delivery device according to claim 7, wherein the cut-out section comprises a radially extending first side wall configured to provide a step-change in a radius of the retaining member that defines an engaging portion.

9. The medicament delivery device according to claim 2, wherein the drive mechanism further comprises a drive member configured to move the plunger rod from a proximal position to a distal position under a force of the drive member, wherein the needle cover retaining mechanism is in the first state when the plunger rod is in the proximal position and the distal position and in the second state for at least a majority of a length of a plunger rod stroke between the proximal position and the distal position.

10. The medicament delivery device according to claim 9, wherein the plunger rod comprises a slot having a first portion, a second portion, and a third portion extending longitudinally, wherein the first portion and the second portion of the slot are circumferentially offset from one another and are joined by a first connecting portion, and the second portion and the third portion of the slot are circumferentially offset from one another and are joined by a second connecting portion.

11. The medicament delivery device according to claim 10, wherein the retaining member comprises a protrusion located in the slot, the slot and the protrusion being configured to allow relative axial movement between the plunger rod and the retaining member.

12. The medicament delivery device according to claim 11, wherein when the plunger rod is in the proximal position the protrusion of the retaining member is located in the first portion of the slot, and wherein upon the distal movement of the plunger rod from the proximal position the protrusion is moved into the second portion of the slot such that the retaining member is moved from the first state to the second state and rotationally coupled to the plunger rod.

13. The medicament delivery device according to claim 12, wherein when the plunger rod is moved into the distal position, the protrusion of the retaining member is located in the second portion of the slot and the plunger rod is rotatable between a first plunger rod rotational position and a second plunger rod rotational position to move the retaining member from the second state to the first state.

14. The medicament delivery device according to claim 13, wherein the drive mechanism further comprises a drive member housing, the drive member housing comprising a projection located in the slot of the plunger rod, wherein the projection is located in the second portion of the slot for a majority of the plunger rod stroke from the proximal position such that the plunger rod is maintained in the first plunger rod rotational position, and wherein the projection is located in the third portion of the slot when the plunger rod is in the distal position such that the plunger rod is moved to the second plunger rod rotational position.

15. The medicament delivery device according to claim 14, wherein the projection of the drive member housing is located proximally to the protrusion of the retaining member.

16. The medicament delivery device according to claim 14, wherein the drive mechanism further comprises a rotating collar located at least partially within the drive member housing, the rotating collar comprising a threaded surface, wherein the plunger rod comprises a threaded surface configured to cooperate with the threaded surface of the rotating collar, and wherein the drive member comprises a torsion spring.

17. The medicament delivery device according to claim 1, wherein the medicament delivery device is configured to inject greater than 2 ml of medicament and/or wherein the medicament delivery device is configured to inject the medicament having a viscosity of greater than 25 cP.

18. The medicament delivery device according to claim 1, further comprising a needle cover lock configured to prevent proximal movement of the needle cover once the needle cover is in the extended position post-use.

19. The medicament delivery device according to claim 1, wherein the medicament delivery device comprises medicament.

20. A method of temporarily removing a holding force required to operate a medicament delivery device, the method comprising:

moving a needle cover from an extended position, in which the needle cover extends from a distal end of a housing and covers a distal end of a needle, to a retracted position, in which the needle protrudes from a distal end of the needle cover, against a force of a needle cover biasing member;

moving a plunger rod of the medicament delivery device distally to (i) cause a retaining member of a retaining mechanism to rotate from a first state, in which the retaining member is disengaged from the needle cover, to a second state, in which the retaining member engages the needle cover and prevents distal movement of the needle cover under the force of the needle cover biasing member, such that a user is no longer required to counteract the force of the needle cover biasing member and to (ii) cause the retaining member to be rotationally coupled to the plunger rod;

rotating the retaining member from the second state back to the first state to reapply the force of the needle cover biasing member; and moving the needle cover from the retracted position to the extended position.

* * * * *